United States Patent
Sakuth et al.

(10) Patent No.: US 6,881,700 B2
(45) Date of Patent: Apr. 19, 2005

(54) DEALUMINIZED CATALYST CARRIER, METHOD OF PRODUCTION, AND METHOD FOR HYDRATING $C_2$ OR $C_3$ OLEFINS WITH WATER

(75) Inventors: Michael Sakuth, Marl (DE); Dietrich Maschmeyer, Recklinghausen (DE); Gregor Lohrengel, Dorsten (DE); Guido Stochniol, Marl (DE)

(73) Assignee: SASOL Germany GmbH, Hamburg (DE)

( * ) Notice: Subject to any disclaimer, the term of this patent is extended or adjusted under 35 U.S.C. 154(b) by 0 days.

(21) Appl. No.: 10/634,879

(22) Filed: Aug. 6, 2003

(65) Prior Publication Data

US 2004/0029718 A1 Feb. 12, 2004

Related U.S. Application Data

(63) Continuation of application No. 09/720,785, filed as application No. PCT/EP99/04486 on Jun. 29, 1999, now abandoned.

(30) Foreign Application Priority Data

Jul. 3, 1998 (DE) .......................................... 198 29 747

(51) Int. Cl.[7] .............................................. B01J 21/08
(52) U.S. Cl. ........................ 502/263; 502/439; 585/275
(58) Field of Search ............................. 502/80, 81, 83, 502/85, 439, 263; 585/275

(56) References Cited

U.S. PATENT DOCUMENTS

| | | |
|---|---|---|
| 4,548,914 A | 10/1985 | Chu |
| 4,581,215 A | 4/1986 | Kaeding |
| 4,808,559 A | 2/1989 | Sommer et al. |
| 5,208,195 A | 5/1993 | Schlueter et al. |
| 5,288,739 A | 2/1994 | Demmel |
| 5,366,948 A | 11/1994 | Absil et al. |

FOREIGN PATENT DOCUMENTS

| | | |
|---|---|---|
| DE | 1 156 772 | 11/1963 |
| EP | 0 283 649 | 9/1988 |
| EP | 0 503 229 | 9/1992 |
| GB | 1 306 141 | 2/1973 |

OTHER PUBLICATIONS

English language abstract of EP 0 503 229 9/'92.
English language abstract of EP 0 283 649 9/'88.
English Translation of DE 1 156 772 11/'63.
European Patent Office Action, Dated Jul. 18, 2003.
English Translation of BR 7/'03
PCT Preliminary International Examination Report, Dated Aug. 3, 2000.
English Translation of DR 8/00.

*Primary Examiner*—Stanley S. Silverman
*Assistant Examiner*—Edward M. Johnson
(74) *Attorney, Agent, or Firm*—Pillsbury Winthrop LLP

(57) ABSTRACT

A catalyst support comprising silicates is described. This catalyst support has a lower aluminum content than naturally occurring sheet silicates and can be used in the hydration of $C_2$ and $C_3$ olefins to produce $C_2$ and $C_3$ alcohols. A method for the production of the catalyst support and a process for hydrating $C_2$ and $C_3$ olefins are also described. One advantage of this catalyst support is the reduction in aluminum leaching that occurs when this catalyst is used in the presence of phosphoric acid.

33 Claims, 1 Drawing Sheet

DEALUMINIZED CATALYST CARRIER, METHOD OF PRODUCTION, AND METHOD FOR HYDRATING C₂ OR C₃ OLEFINS WITH WATER

This is a continuation of U.S. patent application Ser. No. 09/720,785, filed May 31, 2001 now abandoned, which is the U.S. national stage of PCT/EP99/04486, filed Jun. 29, 1999, which in turn claims priority to German application no. 198 29 747.5, filed Jul. 3, 1998. All applications and incorporated in their entirety herewith by reference.

FIELD OF THE INVENTION

This invention claims a dealuminised catalyst support, a process for producing the catalyst support and a process for hydrating $C_2$ or $C_3$ olefins with water in the presence of a catalyst, which consists of said acid-impregnated catalyst support.

BACKGROUND OF THE INVENTION

It is known that linear or slightly branched olefins of relatively low molecular weight may be reacted in the gaseous phase with water vapour at elevated pressures and temperatures to form alcohols. Of particular industrial significance is the synthesis of ethanol from ethene and isopropanol from propene. Production of these alcohols proceeds in the presence of acidic catalysts, wherein as a rule a phosphoric acid-impregnated, aluminosilicate or silicate material is used as the catalyst support.

The material of the catalyst support either comprises pure silicic acid, such as for example silica gel (U.S. Pat. No. 2,579,601), or consists of silicic acid with varying alumina contents (U.S. Pat. No. 3,311,568) or of pure, for example montmorillonite-containing phyllosilicates (DE 29 08 491).

Apart from these phosphoric acid-containing catalyst supports, zeolite materials (EP 0 323 269 B1) or other acidic catalysts, such as zirconium phosphates (GB 005 534) for example, are also used.

In the case of supports based exclusively on silicic acid in the form of silica gels, mechanical strength over a relatively long service life has so far proved problematic. Aluminium-containing catalyst supports or those based solely on alumina exhibit markedly greater long-term stability but have the considerable disadvantage that aluminium leaches out of the catalyst support through the action of the phosphoric acid during the hydration reaction. The aluminium reappears as a sparingly soluble deposit in the form of aluminium phosphates in the downstream apparatus. These become gradually clogged thereby.

DE 1 156 772 discloses a process for reducing the aluminium content of the phyllosilicates through the action of hydrochloric acid. However, the support material still comprises a residual aluminium content of approximately 1 to 2 wt. % even when washed intensively with hydrochloric acid.

EP 0 578 441 B1 achieves a degree of long-term stability by using a pelletised Aerosil-based silicate support (Degussa) containing no aluminium. The starting material for Aerosil production is silicon tetrachloride, which is relatively expensive. Since phyllosilicate-based materials, such as montmorillonite for example, are natural products which may be excavated from appropriate deposits, they have a clear advantage over pelletised silicate supports from the point of view of the economic viability of the hydration process.

SUMMARY OF THE INVENTION

The object of the present invention is therefore to provide an economically viable process for hydrating $C_2$ or $C_3$ olefins with water in the presence of a catalyst comprising an acid-impregnated catalyst support, with which process the catalyst support exhibits the highest possible long-term stability while at the same time as little aluminium as possible is discharged during the hydration reaction.

DETAILED DESCRIPTION

It has surprisingly been found that a dealuminised catalyst support based on substantially aluminium-containing phyllosilicates of montmorillonite structure, having an aluminium content of less than 0.3 wt. %, exhibits high long-term stability and that, in the case of a process for hydrating $C_2$ or $C_3$ olefins with water in the presence of a catalyst comprising an acid-impregnated catalyst support, no or only small amounts of aluminium are washed out of the catalyst support if the hydration reaction is performed using a dealuminised catalyst support according to at least one of claims 1 to 24.

The present invention therefore provides a dealuminised catalyst support, based on substantially aluminium-containing phyllosilicates of montmorillonite structure, having an aluminium content of less than 0.3 wt. %.

The present invention also provides a process for reducing the aluminium content of a catalyst support comprising substantially aluminium-containing phyllosilicates of montmorillonite structure, characterised in that the catalyst support is
- impregnated with acid,
- treated hydrothermally at a temperature of from 160 to 300° C. and a partial pressure of water vapour of from 4 to 80 $bar_{abs}$,
- then washed with acidic, basic or neutral solution at a temperature of from 20 to 100° C. and
- then rewashed with water until the washing water is neutral.

In addition, the present invention provides a process for hydrating $C_2$ or $C_3$ olefins with water in the presence of a catalyst comprising an acid-impregnated catalyst support according to at least one of claims 1 to 24.

In the context of the present invention, hydration or hydration reaction is understood to mean the reaction of water with a carbon-carbon double bond.

In the context of the present invention, dealuminisation and dealuminised catalyst supports are understood to mean respectively a process for reducing aluminium content or a catalyst support with reduced aluminium content.

By using the process according to the invention, a catalyst support may be produced on the basis of calcined and post-treated phyllosilicates, which exhibits a much lower aluminium content than a catalyst support not treated according to the invention. Despite the lower aluminium content, the catalyst retains its long-term stability. By using the catalyst support according to the invention in the process according to the invention for hydrating $C_2$ or $C_3$ olefins with water, the proportion of aluminium washed out during the hydration reaction is markedly reduced. In this way, fewer sparingly soluble aluminium compounds arise during the hydration reaction, which compounds reduce the service lives of downstream apparatus, such as heat exchangers for example, in conventional processes by clogging the conduits or heat exchange surfaces.

The dealuminised catalyst support according to the invention, with an aluminium content of less than 0.3 wt. %, contains substantially aluminium-containing phyllosilicates. The dealuminised catalyst support according to the invention particularly preferably has an aluminium content of less than 0.03 wt. %. The aluminium-containing phyllosilicates are preferably smectites and preferably exhibit a montmorillonite structure. Bentonites are an example of phyllosilicates which comprise substantially aluminium-containing phyllosilicates of montmorillonite structure. In addition to montmorillonites, the bentonites may contain as further constituents for example mica, illite, cristobalite and zeolites.

Commercially available catalyst supports, for example based on calcined and post-treated phyllosilicates, constitute the starting materials for producing the catalyst support according to the invention.

The dealuminised catalyst support according to the invention having an aluminium content of less than 0.3 wt. %, preferably less than 0.03 wt. %, based on substantially aluminium-rich phyllosilicates of montmorillonite structure, may be obtained by impregnation of the catalyst support with an acid, preferably a mineral acid and particularly preferably a phosphoric acid, preferably a 10 to 90 wt. % phosphoric acid, particularly preferably a 50 to 60 wt. % phosphoric acid, such that the catalyst support contains from 5 to 60%, preferably 30 to 40% of an acid, preferably a phosphoric acid, subsequent hydrothermal treatment at a temperature of from 160 to 300° C., preferably a temperature of from 220 to 260° C. and a partial pressure of water vapour of from 4 to 80 $bar_{abs}$, preferably at a partial pressure of water vapour of from 16 to 25 $bar_{abs}$, subsequent washing with acidic, basic or neutral, preferably acidic or neutral solution, particularly preferably with water, hydrochloric acid or water, containing 0 to 30 parts concentrated hydrochloric acid, at a temperature of from 20 to 100° C., preferably of from 70 to 90° C., and subsequent rewashing of the catalyst support until the washing water is neutral.

An exemplary embodiment of the process according to the invention for reducing the aluminium content of a catalyst support is described below, without the process according to the invention being restricted thereto.

To reduce the aluminium content of a catalyst support, which comprises substantially aluminium-containing phyllosilicates, commercially available catalyst supports containing phyllosilicates, such as montmorillonites or bentonites for example, may be used. The catalyst supports preferably take the form of spherical bodies, such as balls, lenses, cuboids, cylinders, or indeed of irregular shapes, but they particularly preferably take the form of balls. The spherical bodies preferably exhibit an average diameter of from 1 to 10 mm, particularly preferably one of 4 to 6 mm.

To reduce the aluminium content in the catalyst support, the catalyst support is impregnated in acid, treated hydrothermally, then washed and finally rewashed.

To achieve the effect according to the invention, the catalyst support is impregnated in acid, preferably in a mineral acid and very particularly preferably in phosphoric acid. A 10 to 90 wt. % phosphoric acid, preferably a 50 to 60 wt. % phosphoric acid is used. After impregnation, the catalyst support should exhibit an acid content, preferably a phosphoric acid content, of from 5 to 60 wt. %, preferably 30 to 40 wt. %. The catalyst support is then treated hydrothermally.

Under hydrothermal conditions, phyllosilicate materials, such as montmorillonite for example, convert into cristobalite-like structures. At the same time, the micropores originally present disappear. These morphological structural changes are clearly visible in the BET surface area, the pore volume and the pore radius distribution.

Under the hydrothermal reaction conditions, so-called "open" pore structures are obtained.

The hydrothermal treatment of the phyllosilicate-containing catalyst support may be performed at temperatures of between 160 and 300° C. and a partial pressure of water vapour of between 4 and 80 $bar_{abs}$, preferably between 220 and 260° C. and a partial pressure of water vapour of from 16 to 25 $bar_{abs}$.

After the hydrothermal treatment, the catalyst support is washed with a basic, acidic or neutral solution, preferably with an acidic or neutral solution, particularly preferably with hydrochloric acid, with water containing from 0 to 30 parts concentrated hydrochloric acid or with a neutral aqueous solution. Washing of the catalyst support is performed at a temperature of from 20 to 100° C., preferably from 70 to 90° C.

After washing, the catalyst support may be washed with water until the washing water is neutral.

The catalyst supports comprise a total pore volume of from 0.2 to 0.9 ml/g, particularly preferably between 0.6 and 0.7 ml/g. The compressive strength of the catalyst supports should be at least 10 N/mm, preferably at least 20 N/mm.

In a particular embodiment of the process according to the invention, the hydrothermal treatment of the acid-impregnated catalyst support, which contains from 5 to 60 wt. %, preferably 30 to 40 wt. % phosphoric acid, proceeds through use as a catalyst in a hydration reaction of $C_2$ or $C_3$ olefins. To impregnate the catalyst support, a 10 to 90 wt. % phosphoric acid is preferably used, particularly preferably a 50 to 60 wt. % phosphoric acid.

In this hydration reaction, olefin and water in a molar ratio of 0.1 to 0.8, preferably 0.15 to 0.5, are caused to react in a reactor, preferably a tubular reactor, filled with the catalyst. The olefin used and the water used are introduced into the reactor in gaseous or liquid, preferably gaseous, form. To evaporate the water or heat the two educts to reaction temperature, it may be advantageous to convey the two educts into the reactor via an evaporator and/or thermostatting section, which is/are heated to the reaction temperature electrically or by means of heat-transfer media. The gas hourly space velocity (GHSV) should amount to between 10 and 100 $l_n/min/l_{Cat}$. The hydration reaction is performed at a temperature of from 160 to 300° C. and a pressure of from 20 to 200 $bar_{abs}$. Hydration of ethene to yield ethanol is preferably performed at a temperature of from 220 to 260° C. and a pressure of from 60 to 80 $bar_{abs}$.

The reactor outlet may preferably be connected with a cooler, which condenses out a major part of the subcritical components and makes these available to further working-up stages, e.g. separation by distillation.

To monitor the activity and selectivity of the acid-impregnated catalyst support, it may be advantageous to analyse the exit stream from the reactor. Analysis may proceed by gas chromatography, for example.

To extend the service life of the catalyst, it may be advantageous to add more of the acid with which the catalyst support was impregnated to the reactor continuously or discontinuously, preferably continuously. Introduction of the acid into the reactor may be performed by injection, for example. The amount of acid which is introduced into the reactor may be made to depend on the result of analysis of the exit stream. Analysis of the exit stream and determination of the resultant acid quantity which is added may be performed automatically.

After hydrothermal treatment of the catalyst support, through use as a catalyst in a hydration reaction, the residual acid with which the catalyst support was impregnated is removed by washing with water until the washing water is neutral.

After removal of the residual acid, the catalyst support is washed with a basic, acidic or neutral solution, preferably with an acidic or neutral solution, particularly preferably with hydrochloric acid, with water containing 0 to 30 parts concentrated hydrochloric acid or with a neutral aqueous solution. The catalyst support may be washed at a temperature of from 20 to 100° C., preferably at a temperature of from 70 to 90° C.

After washing, the catalyst support may be rewashed with water until the washing water is neutral.

In the case of catalyst supports which have been treated hydrothermally through use as a catalyst in a hydration reaction, it may be advantageous, after reduction of the aluminium content in the catalyst support, to clean the catalyst support by burning off any adherent carbon-containing compounds at 300 to 1000° C., preferably at 450 to 500° C.

In both embodiments of the process according to the invention, a treated catalyst support is obtained with a reduced aluminium content. The treated catalyst supports have an average diameter of from 1 to 10 mm, preferably from 4 to 6 mm. The total pore volume amounts to from 0.2 to 0.9 ml/g, preferably from 0.6 to 0.7 ml/g. The compressive strength after treatment of the catalyst support amounts to at least 10 N/mm, preferably at least 20 N/mm. The aluminium content of the treated catalyst support is less than 0.3 wt. %, preferably less than 0.03 wt. %.

The catalyst supports having reduced aluminium content produced by the process according to the invention may be used to produce catalysts.

The catalyst supports having reduced aluminium content produced by the process according to the invention may be used according to the invention in the hydration of $C_2$ or $C_3$ olefins with water in the presence of a catalyst comprising an acid-impregnated catalyst support treated according to the invention.

The catalyst support is preferably impregnated with an acid, preferably phosphoric acid. To achieve maximum catalyst activity, the phosphoric acid content of the impregnated catalyst support should be between 5 and 60 wt. %, preferably between 30 and 40 wt. %. To impregnate the catalyst support, an aqueous phosphoric acid solution is used with a phosphoric acid content of from 10 to 90 wt. %, preferably from 50 to 60 wt. %. The acidic catalyst thus produced is introduced into a reactor, preferably a tubular reactor. The reactor is operated isothermally or non-isothermally, preferably isothermally, and may be heated electrically or by means of heat-transfer media.

The reactor is supplied continuously or discontinuously, preferably continuously, with the educts water and $C_2$ or $C_3$ olefin. The ratio of water to olefin with which the educts are fed into the reactor is adjusted to a molar ratio of from 0.1 to 0.8, preferably from 0.15 to 0.5. Adjustment of the molar ratio may be effected for example by means of mass flow rate regulators. The two educts may be fed into the reactor in liquid or gaseous, preferably gaseous, form. To evaporate the water or to heat the two educts to reaction temperature, it may be advantageous to convey the two educts into the reactor via an evaporator and/or thermostatting section, which is/are heated to the reaction temperature electrically or by means of heat-transfer media. The temperature in the reactor and the temperature at which the educts flow into the reactor amounts to from 160 to 300° C. During hydration of ethene to yield ethanol, the temperature in the reactor and the temperature at which the educts flow into the reactor is 220 to 260° C.

The pressure in the reactor is adjusted to within the range of from 20 to 200 $bar_{abs}$, preferably from 60 to 80 $bar_{abs}$.

The reactor output is preferably connected with a cooler which condenses out a major part of the subcritical components and feeds these to further working-up stages.

To monitor the activity and selectivity of the acid-impregnated catalyst support, it may be advantageous to analyse the exit stream from the reactor. Analysis may proceed by gas chromatography, for example.

To extend the service life of the catalyst, it may be advantageous to introduce the acid preferably phosphoric acid, with which the catalyst support was impregnated into the reactor continuously or discontinuously, preferably continuously. Introduction of the acid into the reactor may be performed by injection, for example. The amount of acid which is introduced into the reactor may be made to depend on the result of analysis of the exit stream. Analysis of the exit stream and determination of the resultant acid quantity which is added may be performed automatically.

BRIEF DESCRIPTION OF THE FIGURES

FIG. 1

FIG. 1 shows the reaction rate of ethene in a hydration reaction as a function of the test running time. The measured values from four tests are reproduced. The measured values denoted with circles show the reaction rate of ethene relative to running time, if a new catalyst support with the original aluminium content is used. The reaction rate measurement points represented as squares stem from three series of tests performed using a catalyst support with reduced aluminium content.

FIG. 2

FIG. 2 shows the rate of formation of ethanol in a hydration reaction as a function of test running time. The measured values from four tests are reproduced. The measured values denoted with circles show the rate of formation of ethanol relative to running time, if a new catalyst support with the original aluminium content is used. The measurement points for rate of ethanol formation represented as squares stem from three series of tests performed using a catalyst support with reduced aluminium content.

Figure 1:
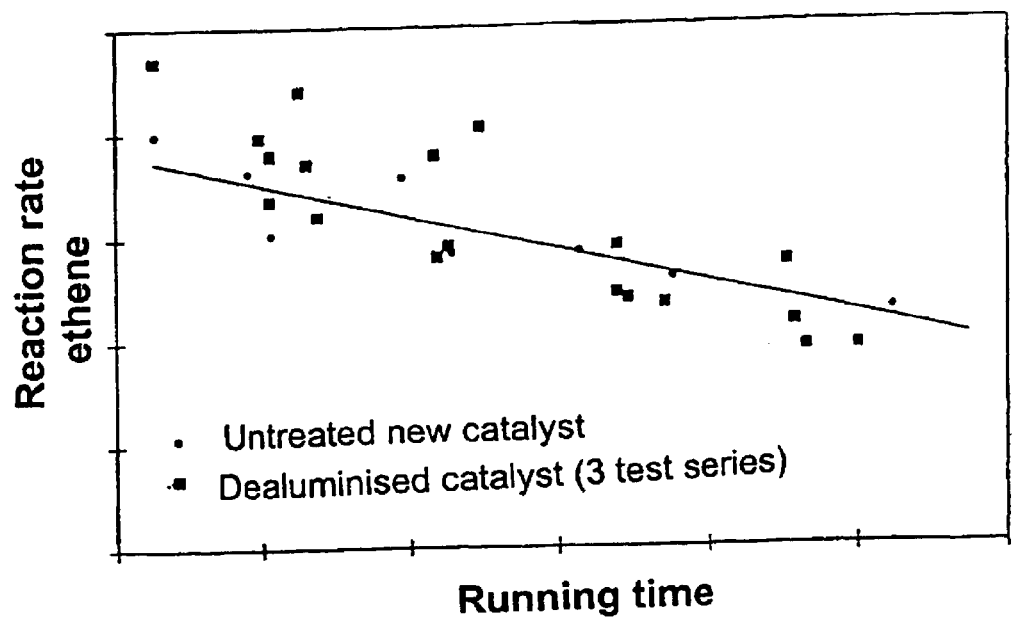
FIGS. 1 and 2 show reaction rates for ethene and rates of formation for ethanol using variously treated catalyst supports as a function of test running times, without the process according to the invention being limited to these results.

The process according to the invention is described with reference to the following Examples, without being limited thereto.

EXAMPLE 1

Ethanol Synthesis with an Untreated Catalyst Support

The test was performed in a pilot installation, which has as its core component an isothermally operated tubular reactor 1000 mm in length and 48 mm in diameter.

The educts water and ethene are fed to the reactor via an evaporator or thermostatting section heated electrically to the reaction temperature. The water is added in liquid form via a pump, while the ethene is taken from 130 bar steel cylinders. The feed stream comprising a 0.3:1 mixture of ethene and water (molar basis) is adjusted by means of a mass flow rate regulator.

The reactor output is connected with a cooler, in order to condense out the major part of the subcritical components, substantially ethanol, water and diethyl ether; the rest passes into the waste gas, the volumetric flow rate of which may be determined using a gas meter. Some of the waste gas is fed to a gas chromatograph via a bypass stream. The discharged liquid likewise undergoes analysis by gas chromatograph.

In the present Example, ethanol synthesis was measured at 240° C. and 70 bar$_{abs}$. The standard test conditions are summarised in Table 1. The catalyst used was an untreated new catalyst support, KA-1 made by Südchemie AG. The characteristics of the support are listed in Table 2. The conversion and selectivity values achieved at the start of the test are likewise contained in Table 2.

To determine the aluminium content of the catalyst support, the latter was analysed with an atomic emission spectrometer before the test was performed, to determine the aluminium content. The atomic emission spectrometer used was an inductively coupled plasma atomic emission spectrometer (ICP-AES) JY 38+made by ISA Jobin Yvon. The results of the analysis are reproduced in Table 2.

EXAMPLE 2

Ethanol Synthesis with an Untreated Old Support

The test was repeated as described in Example 1. This time, an untreated catalyst support already used once to catalyse a hydration reaction (old support) was used as catalyst support. Once again, the standard test conditions indicated in Table 1 apply. The test results and the characteristics of the catalyst support are similarly reproduced in Table 2.

As may be inferred from the values in Table 2, the specific surface area of the impregnated catalyst support diminishes after use once as a catalyst. Similarly, the aluminium content is reduced to approx. ¼ of the original aluminium content after use once as a catalyst. The remaining ¾ of the original aluminium content of the untreated new support was washed out of the catalyst support during the hydration reaction. This aluminium forms the sparingly soluble residues which have proven to be a hindrance in subsequent working-up stages.

EXAMPLE 3

Ethanol Synthesis with a Treated Id Support

The test was repeated as described in Example 1. The catalyst support used was a used old support, whose aluminium content was reduced by treatment by the process according to the invention. Once again, the standard test conditions indicated in Table 1 apply. The test results and the characteristics of the catalyst support are similarly reproduced in Table 2.

Figure 2:
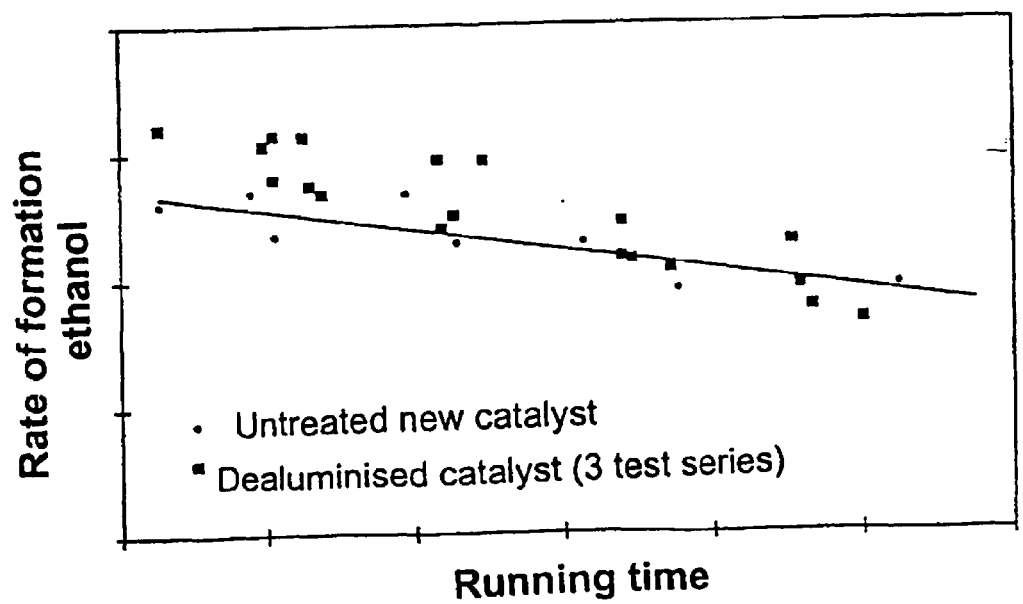

The deactivation behaviour of a catalyst support without reduced aluminium content and of one with reduced aluminium content is shown in FIG. 1 and FIG. 2.

As is clear from Table 2, the aluminium content of the catalyst support has been reduced to less than 0.03 wt. % by treating the old support by the process according to the invention. This value represents the detection limit of the atomic emission spectrometer used. At 30 N/mm, the compressive strength of the treated old support is still sufficient to ensure good long-term stability of the catalyst support. Despite treatment of the catalyst support and reduction of the aluminium content to less than 0.03 wt. %, ethylene conversion and ethanol yield remained just as good as in the case of the untreated, unused catalyst support (new support) or the untreated old support, indeed in the present test they were even slightly better.

As may be inferred from FIGS. 1 and 2, reduction of the aluminium content by the process according to the invention does not have any effect on the ethene reaction rate and the rate of ethanol formation.

TABLE 1

| Standard test conditions | |
| --- | --- |
| Process parameters | Value of process parameter |
| Total pressure during reaction | 70 bar$_{abs.}$ |
| Reactor temperature (isothermal) | 240° C. |
| GHSV | 21.3 l$_N$/min/l$_{Cat.}$ |
| Water-to-ethylene ratio | 1.0:0.3 mol:mol |
| Support material | KA-1 (Südchemie) |

TABLE 2

| Property (impregnated support) | New support | Untreated old support | Treated old support |
| --- | --- | --- | --- |
| Compressive strength | 20 N/mm | 40 N/mm | 30 N/mm |
| Spec. surface area (BET) | 20 m²/g | 4 m²/g | 3 m²/g |
| Pore volume$_{total}$ | 0.7 ml/g | 0.4 ml/g | 0.4 ml/g |
| Al content | 1.3 wt. % | 0.31 wt. % | <0.03 wt. % |
| Si content | 25 wt. % | 25 wt. % | 24 wt. % |
| H$_3$PO$_4$ content | 35 wt. % | 36 wt. % | 35 wt. % |
| Ethylene conversion at start of test | 5% | 5% | 6% |
| Space-time yield (ethanol) at start of test | 77.4 g/l$_{Cat}$/h | 76.4 g/l$_{Cat}$/h | 79.8 g/l$_{Cat}$/h |

What is claimed is:

1. A process for the production of a catalyst support with an aluminum content of less than 0.3 wt. %, the process comprising:
   a) impregnating a phyllosilicate of montmorillonite structure with acid;
   b) hydrothermally treating the phyllosilicate at a temperature of from 160° C. to 300° C. and water vapor at a partial pressure of from 4 to 80 bar$_{abs}$;
   c) washing the phyllosilicate with an aqueous solution at a temperature of from 20° C. to 200° C. until the solution obtained after washing is neutral.

2. The process according to claim 1, wherein the aqueous solution is acidic.

3. The process according to claim 2, wherein the aqueous solution comprises a solution of hydrochloric acid.

4. The process according to claim 3, wherein the solution of hydrochloric acid contains 1 to 30 parts of hydrochloric acid.

5. The process according to claim 1, wherein the aqueous solution is basic.

6. The process according to claim 1, wherein the aqueous solution is neutral.

7. The process according to claim 1 further comprising:
   d) cleaning the catalyst by burning off organic carbon compounds at a temperature of from 300° C. to 1000° C.

8. The process according to claim 1, wherein the washing is at a temperature of from 70° C. to 90° C.

9. The process according to claim 1, wherein the acid is a mineral acid.

10. The process according to claim 1, wherein the acid is phosphoric acid.

11. The process according to claim 10, wherein the catalyst is impregnated with 10 wt. % to 90 wt. % of phosphoric acid.

12. The process according to claim 11, wherein the catalyst is impregnated with 30 wt. % to 40 wt. % of phosphoric acid.

13. The process according to claim 11, wherein the catalyst is impregnated with 50 wt. % to 60 wt. % of phosphoric acid.

14. A process for the production of a catalyst support with an aluminum content of less than 0.03 wt. %, the process comprising:
   a) impregnating a phyllosilicate of montmorillonite structure with acid;
   b) hydrothermally treating the phyllosilicate at a temperature of from 160° C. to 300° C. and water vapor at a partial pressure of from 4 to 80 $bar_{abs}$;
   c) washing the phyllosilicate with an aqueous solution at a temperature of from 20° C. to 200° C. until the solution obtained after washing is neutral.

15. A process for the hydration of $C_2$ or $C_3$ olefins comprising reacting the $C_2$ or $C_3$ olefin with water in the presence of a catalyst support with an aluminum content of less than 0.3 wt. %, wherein the catalyst is produced by a process comprising:
   a) impregnating a phyllosilicate of montmorillonite structure with acid;
   b) hydrothermally treating the phyllosilicate at a temperature of from 160° C. to 300° C. and water vapor at a partial pressure of from 4 $bar_{abs}$ to 80 $bar_{abs}$; and
   c) washing the phyllosilicate with an aqueous solution at a temperature of from 20° C. to 200° C. until the solution obtained after washing is neutral.

16. The process according to claim 15, wherein the $C_2$ or $C_3$ olefins and the water are in a gaseous state.

17. The process according to claim 15, wherein the $C_2$ or $C_3$ olefins and the water are in a molar ratio of from 0.1 to 0.8.

18. The process according to claim 15, conducted at a temperature of from 170° C. to 300° C.

19. The process according to claim 15, conducted at a pressure of from 20 $bar_{abs}$ to 200 $bar_{abs}$.

20. The process according to claim 15, wherein the acid is phosphoric acid.

21. The process according to claim 15, wherein the acid is a mineral acid.

22. The process according to claim 15, wherein the process is conducted in a reactor.

23. The process according to claim 22, wherein the $C_2$ or $C_3$ olefins and the water are introduced into the reactor in a gaseous state.

24. A process for the hydration of $C_2$ or $C_3$ olefins comprising reacting gaseous $C_2$ or $C_3$ olefin with gaseous water in a reactor in the presence of a catalyst support with an aluminum content of less than 0.3 wt. %, wherein the catalyst is produced by a process comprising:
   a) impregnating a phyllosilicate of montmorillonite structure with acid;
   b) hydrothermally treating the phyllosilicate at a temperature of from 160° C. to 300° C. and water vapor at a partial pressure of from 4 $bar_{abs}$ to 80 $bar_{abs}$; and
   c) washing the phyllosilicate with an aqueous solution at a temperature of from 20° C. to 200° C. until the solution obtained after washing is neutral;

wherein:
   a) the $C_2$ or $C_3$ olefin and the water are in a molar ratio of from 0.1 to 0.8;
   b) the catalyst comprises from 5 wt. % to 60 wt. % of the acid; and
   c) the hydration is conducted at a temperature of from 170° C. to 300° C. and a pressure of from 20 $bar_{abs}$ to 200 $bar_{abs}$.

25. The process according to claim 24, wherein the acid is phosphoric acid.

26. The process according to claim 24, wherein the $C_2$ or $C_3$ olefin is ethane, the hydration temperature is from 220° C. to 260° C., and the pressure is from 60 $bar_{abs}$ to 80 $bar_{abs}$.

27. The process according to claim 24, wherein the aluminum content is less than 0.03 wt. %.

28. A catalyst support comprising phyllosilicates of montmorillonite structure having an aluminum content of less than 0.3 wt.%, a total pore volume of from 0.2 mL/g to 0.9 mL/g, and a compressive strength of at least 10 N/mm.

29. The catalyst support according to claim 28, wherein the total pore volume is from 0.6 mL/g to 0.7 mL/g.

30. The catalyst support according to claim 28, wherein the compressive strength is at least 20 N/mm.

31. The catalyst support according to claim 28 shaped spherical shape with a diameter of from 1 mm to 10 mm.

32. The catalyst support according to claim 31, wherein the diameter is from 4 to 6 mm.

33. The catalyst support according to claim 28, wherein the aluminum content is leass than 0.3 wt.%.

* * * * *